(12) United States Patent
Strozyk et al.

(10) Patent No.: US 10,736,664 B2
(45) Date of Patent: Aug. 11, 2020

(54) PLATE DISTRACTOR AND ASSEMBLY OF SUCH A PLATE DISTRACTOR AND AN ACTIVATION TOOL

(71) Applicants: ECOLE NATIONALE SUPÉRIEURE DE TECHNIQUES AVANCÉES, Palaiseau (FR); ECOLE POLYTECHNIQUE, Palaiseau (FR); UNIVERSITÉ PARIS DESCARTES, Paris (FR); ASSISTANCE PUBLIQUE—HÔPITAUX DE PARIS, Paris (FR)

(72) Inventors: Hervé Strozyk, L'hôpital (FR); Jean Boisson, Paris (FR); Lahcen Cherfa, Brétigny-sur-Orge (FR); Natacha Kadlub, Paris (FR); Arnaud Picard, Paris (FR)

(73) Assignee: ECOLE NATIONALE SUPERIEURE DE TECHNIQUES AVANCEES, Palaiseau (FR)

( * ) Notice: Subject to any disclaimer, the term of this patent is extended or adjusted under 35 U.S.C. 154(b) by 21 days.

(21) Appl. No.: 16/060,689

(22) PCT Filed: Dec. 9, 2016

(86) PCT No.: PCT/EP2016/080481
§ 371 (c)(1),
(2) Date: Jun. 8, 2018

(87) PCT Pub. No.: WO2017/097998
PCT Pub. Date: Jun. 15, 2017

(65) Prior Publication Data
US 2018/0360497 A1    Dec. 20, 2018

(30) Foreign Application Priority Data
Dec. 9, 2015   (FR) ...................... 15 62069

(51) Int. Cl.
*A61B 17/66* (2006.01)
*A61B 17/68* (2006.01)
*A61B 17/80* (2006.01)

(52) U.S. Cl.
CPC ............ *A61B 17/663* (2013.01); *A61B 17/66* (2013.01); *A61B 17/808* (2013.01); *A61B 2017/681* (2013.01)

(58) Field of Classification Search
CPC ..... A61B 17/7016; A61B 17/80; A61B 17/66; A61B 17/663
See application file for complete search history.

(56) References Cited

U.S. PATENT DOCUMENTS 10,517,643 B2 * 12/2019 Pool ................... A61B 17/7016
2008/0108995 A1    5/2008 Conway
(Continued)

FOREIGN PATENT DOCUMENTS

| WO | 9951160 A1 | 10/1999 |
|----|------------|---------|
| WO | 0178614 A1 | 10/2001 |

(Continued)

OTHER PUBLICATIONS

International Search Report, PCT/EP2016/080481.

*Primary Examiner* — David W Bates
(74) *Attorney, Agent, or Firm* — McNees Wallace & Nurick LLC (57) ABSTRACT

The invention relates to a plate distractor, particularly a maxillofacial plate distractor, comprising a first (12) and a second (14) fixing plate, a threaded pin (24) mounted in a freely rotatable and translatably fixed manner in relation to the first fixing plate (14), a screwed tube (26) fixed to the second fixing plate (12), a permanent magnet (20) extending in a main direction, which is magnetised transversely to the main direction and mounted in the plate distractor (10) such that the rotation of the magnet (20) on itself, about an axis (Continued)

of rotation (D) parallel to the main axis, causes a relative rotation of the threaded pin (24) in relation to the screwed tube (26), the magnet (20) being arranged close to one of the ends of the plate distractor (10).

24 Claims, 5 Drawing Sheets (56) References Cited

U.S. PATENT DOCUMENTS

| | | | |
|---|---|---|---|
| 2012/0179215 A1* | 7/2012 | Soubeiran | A61B 17/7014 606/86 R |
| 2014/0128868 A1* | 5/2014 | Harrison | A61B 17/66 606/60 |

FOREIGN PATENT DOCUMENTS

| | | |
|---|---|---|
| WO | 2007144489 A2 | 12/2007 |
| WO | 2008003952 A1 | 1/2008 |

* cited by examiner

PLATE DISTRACTOR AND ASSEMBLY OF SUCH A PLATE DISTRACTOR AND AN ACTIVATION TOOL

The present invention relates to a plate distractor, in particular a maxillofacial plate distractor. The invention also concerns an assembly of such a distractor and an activation tool of the distractor.

In certain clinical situations, delayed or absent mandibular growth requires surgery in order to extend the mandible. In order to avoid interfering with or blocking natural growth, bone distraction is carried out. This surgical technique allows progressive elongation of the bones. For this purpose, surgical resection or fracturing of the bone, referred to as an osteotomy, is first carried out, and two plates of a plate distractor are then attached to the bone on either side of the osteotomy. A worm gear device makes it possible to control the degree of separation between the plates and thus lengthen the mandible.

The method is known of coupling the worm gear device to an articulated rod in order to more easily control separation of the plates by rotating said rod. However, the distractor with the articulated rod remains in the mouth throughout the treatment period, which may interfere with eating, injure the mucous membranes, and/or make closing of the mouth difficult.

Moreover, the articulated rod has to penetrate the skin or the mucous membrane in order to be manipulated. This solution therefore involves the risk of infectious complications, in particular because it involves contact between the bone and the external environment.

A plate distractor in which separation of the plates is controlled by a magnetic system is known from WO 99/51160.

A plate distractor comprising two plates, the separation of which is controlled by means of a permanent magnet that is connected to the plates by a screw and caused to rotate by a rotary magnetic actuator arranged laterally in relation to the permanent magnet, is known from international application WO 2008/003952. The two plates are held in a fixed position by two parallel rods along which they may slide. Such an arrangement of the magnetic actuator in relation to the permanent magnet exerts a transverse force on the plates via the intermediary of the permanent magnet, which may cause the plates to be pulled loose from the bone to which they are attached. In fact, a magnetic distractor is designed to resist longitudinal forces, but shows weaker resistance to transverse forces. In such a device, moreover, the rotary elements of the distractor, specifically the permanent magnet and the screw, are not protected from their environment. Tissue adherences may therefore occur, and they may be pulled loose when the plate distractor is actuated.

The object of the invention is therefore to provide a plate distractor, in particular a maxillofacial plate distractor, that does not have the above-mentioned drawbacks.

It should be noted that in addition to plate distractors that are attached to the bones to be treated, there are also distractors referred to as centromedullary distractors that are inserted into the bone to be treated.

The method is known of effecting extension of the centromedullary distractor by means of cooperation of a magnet integrated into the centromedullary distractor and a magnet outside the patient, with rotation of the magnet in the distractor effecting the rotation of the worm gear device.

Application WO-A-0178614 describes an example of such a centromedullary distractor. In this document, an electromagnet is arranged completely surrounding the bone to be treated. This electromagnet is actuated in order to generate a magnetic field that causes rotation of the magnet inserted into the centromedullary distractor. However, such a solution is difficult to implement for a maxillofacial distractor, because the electromagnet would have to move around the patient's head. More generally, this solution is not suitable for a plate distractor attached to one side of a bone. In fact, in this case, the action of the magnetic field on the magnet in the distractor would vary depending on the angle of the magnetic field. This would cause variations in torque during a single rotation of the worm gear system. Effecting the extension of such a distractor would therefore be complex. In this configuration, moreover, the interaction force between the magnets is perpendicular to the plane of the plates. This interaction force thus exerts stress on the screw attaching the plates to the bone in the direction perpendicular to the plane of the plates. This increases the risk that the plates may be pulled loose from the bone to which they are attached.

The invention provides a plate distractor, in particular a maxillofacial plate distractor, comprising:
- a first and a second fixing plate,
- a threaded rod,
- a threaded tube mounted on the threaded rod and attached to the second fixing plate,
- a sleeve accommodating the threaded rod that is freely rotatable and translatably attached on the one hand and the threaded tube that is freely translatable and rotatably attached on the other,
- a permanent magnet accommodated in a hermetically sealed housing, extending in a main direction and magnetized transverse to the main direction, mounted in the plate distractor such that the rotation of the magnet on itself around an axis of rotation parallel to the main axis causes a relative rotation of the threaded rod in relation to the threaded tube, with the magnet being located at a distance from one of the ends of the plate distractor, measured in the direction of the axis of rotation of the magnet, of less than or equal to 15 mm, preferably less than or equal to 10 mm, more preferably less than or equal to 5 mm.

According to the invention, the rotation of the threaded rod in relation to the threaded tube causes movement of the latter along the threaded rod, which allows the distance between the second plate and the first plate to be extended.

Advantageously, therefore, the extension of the plate distractor may be controlled from outside the patient, without any contact and without using an activator that pierces the skin or mucosa. It is no longer necessary to use an articulated rod that passes through the tissues of the patient. The plate distractor according to the invention thus causes less discomfort.

Moreover, it is possible to control the extension of the plate distractor according to the invention by means of an activation tool comprising for example a cylindrical magnet magnetized transverse to the axis of this cylindrical magnet of the activation tool. In this case, it is sufficient to place the two magnets opposite each other, as the rotation of the magnet of the activation tool around its axis causes the rotation of the magnet in the plate distractor. It should be noted here that this rotation of the magnet in the distractor is achieved without generating any tensile force on the screws securing each plate perpendicularly to the plate.

It is particularly advantageous that the magnet is arranged close to one end of the plate distractor in order to facilitate the interaction between the magnet in the plate distractor and the magnet in the activation tool.

The presence of the sleeve makes it possible to protect the threaded tube from the external environment and the threaded rod, which improves the safety of the plate distractor during use on the patient.

The presence of the hermetically sealed housing makes it possible to insulate the magnet from the human body and to prevent the magnet from becoming demagnetized during production of the plate distractor under the action of the high welding temperatures of the elements among themselves.

Moreover, because of the magnetization directions of the two magnets, any attractive or repulsive force between these two magnets is reduced compared to a configuration in which the magnets interact along the direction of their magnetization axes. In this manner, the stresses generated by the plate distractor on the bone to which the plate distractor is attached are reduced, and such stresses may cause the plate distractor to be pulled out.

According to preferred embodiments, the plate distractor according to the invention has one or a plurality of the following characteristics, taken individually or in combination:

the magnet is located at one end of the plate distractor;
the magnet has a generally cylindrical shape, in particular a circular or polygonal base, preferably a hexagonal or spherical base;
the plate distractor comprises an angle gear device such that the axis of rotation of the magnet is essentially perpendicular to the axis of the threaded rod and of the threaded tube;
the angle gear device comprises a first gear that is rotationally attached to the magnet and adapted to engage with a second gear controlling the rotation of one of the threaded rod and the threaded tube;
the magnet is connected to the threaded rod or the threaded tube by a reduction device, in particular a geared reduction device;
the reduction device includes, and is preferably composed of, the first and second gears;
the plate distractor comprises an arm connected to the threaded tube, or preferably the threaded rod, by a ball and pin connection and the torque reduction device, with the magnet optionally being attached to the arm;
the ball and pin connection is implemented by means of a universal joint;
the magnet is rotationally attached to the threaded rod or the threaded tube, the magnet preferably being attached to the threaded rod or the threaded tube;
the plate distractor comprises a non-return device that prevents the rotation of the magnet in one direction, controlling a reduction in the distance between the first and second plates, with the non-return device preferably being of the ratchet type;
the magnet is composed of neodymium or neodymium alloy, samarium or samarium alloy, ferrite or ferrite alloy, preferably coated with a biocompatible material;
at least one of, preferably each of the threaded rod, the threaded tube, the first plate and the second plate is/are composed of titanium or titanium alloy;
the first plate is the plate closest to the magnet;
the first plate is the plate farthest from the magnet;
the housing is fixed to the threaded rod;
the housing is freely rotatable in relation to the sleeve;
the magnet is fixed to the housing;
the magnet and the housing are configured such that the magnet is freely rotatable in the housing when it rotates in a first direction and the magnet rotationally drives the housing and thus the threaded rod when it rotates in a second direction, in particular with the magnet comprising an asymmetrical notch and the housing comprising a projection cooperating with the notch such that the magnet turns freely in the first direction and the projection engages with the notch in the second direction;
the sleeve comprises a longitudinal opening having a width essentially equal to the width of the junction between the threaded tube and the second plate for translatably guiding the threaded tube;
the threaded tube has a width less than or equal to the width of the second plate; this limited extension of the threaded tube makes it possible to limit friction, in particular with the sleeve when it moves;
the permanent magnet is such that its magnetization is retained when it is heated to a temperature of 120° C., preferably 130° C., more preferably 134° C.; this makes it possible to sterilize the magnetic distractor while retaining its magnetization;
the threaded rod is mounted in a freely rotatable and translatably fixed manner in relation to the first fixing plate, and in particular, the first plate is fixed in relation to the sleeve;
the threaded rod comprises two longitudinal areas having opposite threads, with the first threaded tube to which the second plate is attached being mounted on one of the two longitudinal areas and a second threaded tube to which the first plate is attached being mounted on the other of the two longitudinal areas. In this manner, the rotation of the threaded rod causes translation of the two threaded tubes in opposite directions, which makes it possible to move the plates away from each other;
the turns of the thread of the first longitudinal area have spacing identical to or different from the turns of the thread of the second longitudinal area. By controlling the spacing between the turns of the thread of the two longitudinal areas, it is thus possible to provide a distractor that allows movement of the plates adapted to the morphology of the patient and the area to be treated;
the plate distractor further comprises a device for determining the extension length of the distractor, in particular of the ratchet type.

According to another aspect, the invention relates to a distraction assembly comprising a plate distractor as described above, in all of its combinations, and an activation tool of the plate distractor comprising a permanent magnet extending in a main direction and magnetized transverse to the main direction, configured to be placed opposite the magnet of the plate distractor.

In this manner, the rotation of the magnet of the activation tool around its main direction causes the rotation of the magnet of the plate distractor around its axis.

According to preferred embodiments, the distraction assembly according to the invention has one or two of the following characteristics, taken individually or in combination:

the magnet of the activation tool is cylindrical, in particular with a circular or polygonal base, preferably a hexagonal or spherical base;
the magnet of the activation tool extends along the longitudinal axis of the plate distractor. This limits the risk of pulling the plate distractor loose;
the activation tool comprises a magnetic shielding housing wherein the magnet is accommodated, with said housing being capable of moving from a closed configuration in which the shielding of the magnetic field is sufficient to prevent the rotation of the magnet of the activation tool around the main direction from causing rotation of the magnet of the plate distractor around its axis to an open configuration in which the rotation of the magnet of the activation tool around the main direction causes the rotation of the magnet of the plate distractor around its axis and vice versa. Such a magnetic shielding housing makes it possible to avoid causing the magnet of the plate distractor to rotate when this is not desired, in particular during the phase in which the activation tool is put into place opposite the magnet of the plate distractor;

the magnetic shielding housing is composed of an alloy having high magnetic sensitivity, for example Permalloy®, or of a ferromagnetic material, in particular a soft ferromagnetic material;

the housing may comprise a diaphragm composed of a magnetic shielding material at its end that is closed when the housing is in a closed configuration and open when the housing is in an open configuration;

the activation tool comprises an opening means for moving the end of the magnetic shielding housing from the closed to the open configuration and vice versa.

According to another aspect, a method is provided for controlling the extension of a plate distractor as described above in all of its combinations by means of an activation tool comprising a permanent magnet magnetized in a transverse direction, comprising the following steps:

i. placing the permanent magnet of the activation tool opposite the permanent magnet of the distractor such that their magnetization directions are essentially parallel; and ii. causing the permanent magnet of the activation tool to pivot on itself around an axis that is essentially colinear with the axis of the permanent magnet of the distractor.

The activation tool may be as described above.

In step i., the end of the magnetic shielding housing is preferably in a closed configuration, with the method comprising a step i'. in which the end of the magnetic shielding housing is moved from the closed configuration to the open configuration.

According to a final aspect, a bone distraction method comprising the following steps is provided:

fracturing of the bone to be lengthened;

fixing of the fixing plates of a plate distractor to the fractured bone such as that described above in all of its combinations, with the fixing plates being attached on either side of the bone fracture; and controlling the extension of the plate distractor using the method for controlling the extension of a plate distractor as described above.

The bone fracture may be carried out in the form of an osteotomy line, in which case the fixing plates are fixed on either side of said osteotomy line.

Other characteristics and advantages of the invention will become apparent on reading the following detailed description, said description referring to the attached drawings, which show the following.

In the following description, elements that are identical or have an identical function have the same reference numbers. For purposes of brevity of the present description, these identical elements are not described in detail for each figure, with only the differences among the various examples being described.

Figure 1:
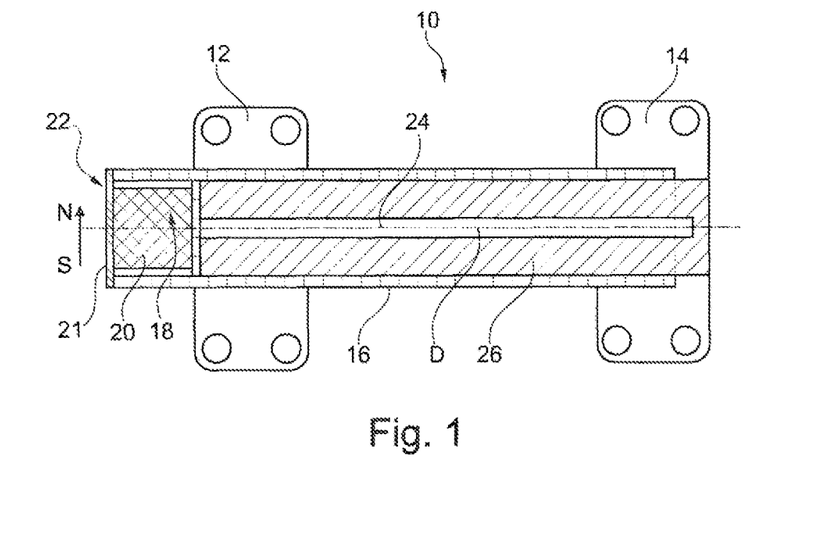
FIG. 1 is a schematic sectional view of a first example of a plate distractor in a collapsed configuration.

FIG. 1 shows a first example of a maxillofacial plate distractor 10.

First of all, this distractor 10 comprises a first 12 and a second 14 fixing plate for fixture to a bone to be treated. These plates 12, 14 are configured to be attached to the treated bone on either side of the fracture. These plates 12, 14 are essentially flat. They may be curved in order to conform to the bone to which they are attached. These plates may have a thickness of less than or equal to 1.6 mm, more favorably 1.2 mm, preferably 1 mm, more preferably less than or equal to 0.6 mm. For example, these plates 12, 14 may be screwed onto the bone to be treated. In particular, the screws used in this case may be composed of titanium, titanium alloy, or a resorbable material. It is generally preferable to use screws made of titanium alloy in combination with resorbable screws. The length of the screws, for example, may be greater than 3 mm and/or less than 10 mm. For example, the screws may have a length of 5 mm. Here, the plates 12, 14 have four holes for positioning four screws. Of course, this number of holes is by no means limitative. For example, one plate may be attached by means of one titanium alloy screw and one screw of plastic resorbable material. The plates have small dimensions, in particular for maxillofacial application, as the available space is small, in order to limit the discomfort caused by the plate distractor. For example, the plates have a length and a width of between 5 and 30 mm respectively.

The first plate 12 is attached to a sleeve 16, for example by welding or bonding. Alternatively, the first plate 12 and the sleeve 16 have a single-piece configuration. Here, the sleeve 16 has a hollow housing 18 at one end accommodating a permanent magnet 20. The magnet 20 is accommodated in a freely rotatable manner around an axis D. The magnet 20 is translatably fixed in relation to the sleeve 16 and thus the first plate 12.

Preferably, the housing 18 is hermetically sealed in order to prevent the magnet 20 from coming into contact with the surrounding environment. Here, this is carried out by fixing a plate 21 that closes the housing 18 after insertion of the magnet 20. In particular, the plate 21 may be welded or bonded. Closing of the housing is particularly advantageous in cases where the magnet 20, composed for example of neodymium or neodymium alloy, samarium or samarium alloy, ferrite or ferrite alloy, is not biocompatible. Alternatively, the magnet 20 may be coated with a biocompatible material, in particular titanium or silicone. In this case, the housing may be open.

Here, the permanent magnet has a cylindrical shape of axis D. More specifically, the magnet 20 has a rotationally symmetrical cross section, in particular a circular cross section. The magnet 20 is magnetized transverse to the axis D. In other words, the north-south orientation of the permanent magnet corresponds to a direction perpendicular to its axis D. Here, the magnet 20 is adapted to pivot around its axis D.

It may be noted here that more generally, the permanent magnet 20 may extend in a main direction and be magnetized transverse to the main direction. In particular, the magnet 20 may thus be cylindrical, either rotationally symmetrical or not, or spherical.

It should also be noted here that the magnet 20 is arranged close to one end of the sleeve 16 and thus the plate distractor 10. Indeed, the permanent magnet is preferably arranged close to one end 22 of the plate distractor 10, in particular at a distance, measured in the direction of the axis D of rotation of the magnet 20, of less than or equal to 15 mm, preferably less than or equal to 10 mm, more preferably less than or equal to 5 mm. According to an embodiment not shown, the magnet 20 is even arranged at the end of the plate distractor. In this case, the end of the plate distractor is formed by one side of the magnet 20.

Here, the magnet 20 is fixed to a threaded rod 24. For example, the threaded rod is bonded to the magnet 20. Alternatively, the magnet 20 and the threaded rod 24 have a single-piece configuration. The threaded rod 24 extends essentially along the axis D of rotation of the permanent magnet. Moreover, the threaded rod 24 is accommodated in a threaded tube 26. The threaded tube 26 is fixed to the second plate 14. For example, the threaded tube 26 is bonded or welded to the second plate 14. Alternatively, the second plate 14 and the threaded tube 26 have a single-piece configuration. The sleeve 16 is hollow, having a cross section complementary to that of the threaded tube 26, such that the threaded tube 26 is partially accommodated in the sleeve 16. The threaded tube 26 is mounted in the sleeve 16 in a sliding manner.

It is to be noted that according to the example of FIG. 1, the axis of rotation of the magnet 20 and the axis of the rod 24 are coincident. This solution is compact and is therefore particularly well-suited for a maxillofacial application, in particular a mandibular application. Moreover, this solution is technically simple. This reduces costs on the one hand and the risk of malfunctioning on the other.

In order to provide biocompatibility and lightness of the plate distractor, at least one of the threaded rod 24, the threaded tube 26, the first plate 12, the second plate 14 and the sleeve 16 is/are composed of titanium or titanium alloy. Preferably, all of these elements are composed of titanium or titanium alloy.

Such a plate distractor may classically be used in a method for bone distraction, in particular distraction of a maxillofacial bone, and more particularly the mandible.

In a first step, a physician makes an osteotomy line for a bone to be lengthened. In this case, one carries out a surgical fracture of the bone to be lengthened.

The physician then fixes the first 12 and second 14 plates of the plate distractor 10 to the bone to be lengthened, on either side of the osteotomy line.

Figure 2:
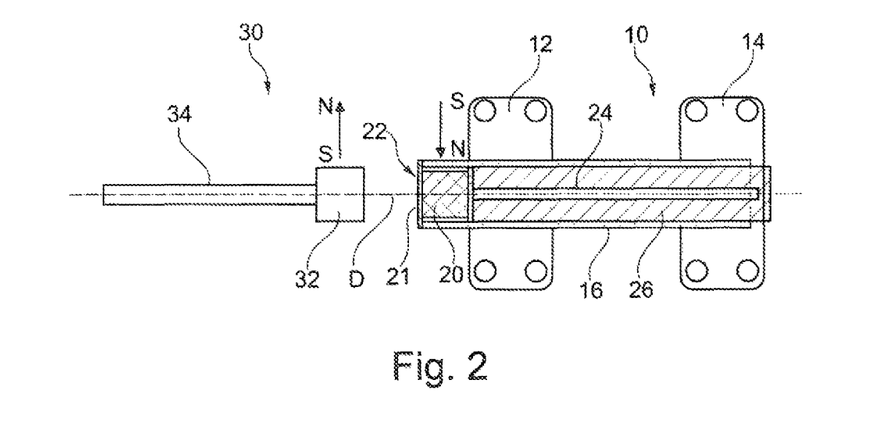
FIG. 2 shows how the extension of the plate distractor of FIG. 1 is controlled by means of an activation tool in a sectional view.

The physician or other user then controls the extension of the plate distractors 10. For this purpose, one may use an activation tool 30, essentially comprising a permanent magnet 32 attached to a rod 34. In the same manner as the magnet 20, the magnet 32 preferably extends in a main direction and is magnetized in a magnetization direction transverse to the main direction. The magnet 32 may be cylindrical, preferably with a rotationally symmetrical cross section, or spherical. Here, the magnet 32 is cylindrical with a circular cross section. Accordingly, the magnet 32 is magnetized in a transverse direction, with the north-south orientation being perpendicular to its main axis.

The controlled extension of the plate distractor 10 is then implemented as follows. In a first step, the magnet 32 is placed opposite the magnet 20. This step can be facilitated, for example, by means of ink marking on the skin of the patient at the time the distractor is put into place. Placement of the magnets 20, 32 opposite one another means that their main axes, i.e. their axes of rotation, are coincident, as shown in FIG. 2. It should be noted here that because of the orientation of magnetization of the two magnets 20, 32, a weak tensile or repulsive force may occur between the magnets. However, this force is weak compared to a case in which the magnets interact in the direction of their axes of magnetization. Moreover, in the case of the example described with respect to FIGS. 1 through 3, this force is essentially parallel to the fixing plates of the distractor. The fixing screws of the plates 12, 14 show considerable resistance to stress in these directions parallel to the plates, thus preventing the distractor from being pulled loose. On the contrary, in cases where these forces are in a direction perpendicular to the plates, as this the case with known distractors, they cause a tensile force to be exerted on the fixing screws of the plates 12, 14. This may cause pain to the patient and even pull loose the plates 12, 14.

Figures 3, 4:
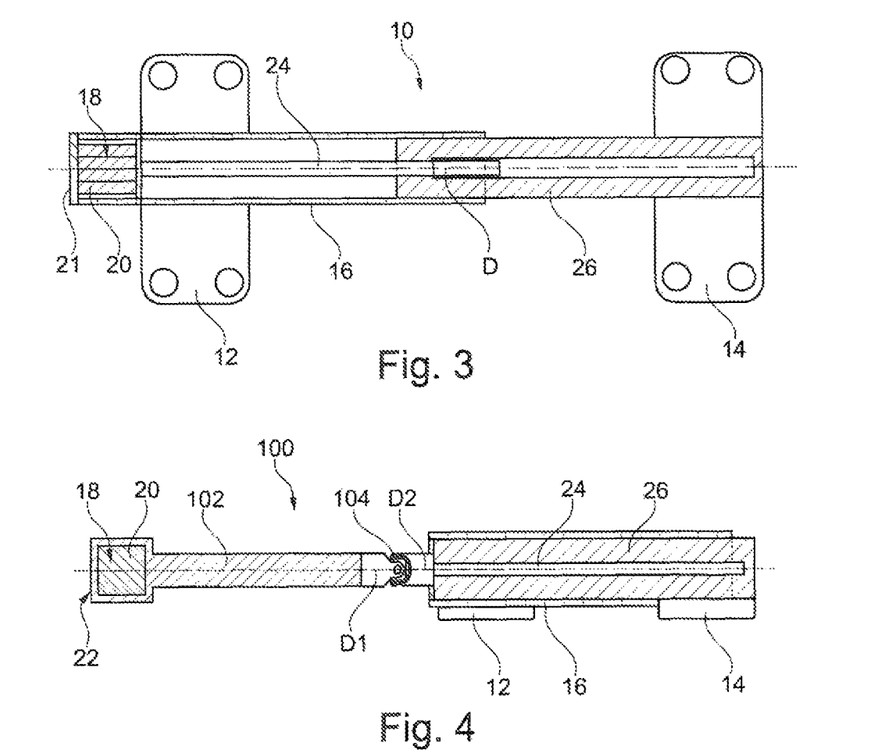
FIG. 3 is a figure similar to FIG. 1 in which the distractor is in an extended configuration.
FIG. 4 is a schematic view of a second example of a plate distractor.

The method for extending the distractor is then carried out by causing the activation tool 30 to rotate on itself around the axis of the magnet 32. One thus causes a rotation of the magnet 20 in the plate distractor 10. As the threaded rod 24 is fixed to the magnet 20, it is also caused to rotate. In contrast, the threaded tube 26 is fixed to the bone to be treated. It therefore cannot pivot. As a result, the rotation of the threaded rod 24 in the threaded tube 26 causes a translational movement of the threaded tube 26 in relation to the sleeve 16. The plate distractor 10 is thus extended, as shown in FIG. 3. In this manner, the distance between the two plates 12, 14 is increased.

It should be noted here that the control tool 30 is particularly simple. Because the extension of the plate distractor 10 is magnetically controlled, this extension can be controlled from outside the patient, in particular from outside the mouth of a patient. The accompanying discomfort is thus sharply reduced. Moreover, this control is implemented by rotation of this tool on itself around the axis of the cylindrical magnet 32. This control can therefore be implemented even in small or difficult-to-access spaces. It is not necessary to use a control tool that has to be arranged completely surrounding the bone to be treated. Moreover, there is no variation in torque during a single rotation of the magnet 32, making it possible to achieve uniform control without any jerkiness.

The plate distractor 100 of FIG. 4 differs from the plate distractor 10 of FIGS. 1 through 3 in that the housing 18 accommodating the magnet 20 is formed into an arm 102, with the magnet 20 being rotationally fixed to the arm 102. Moreover, the arm 102 is connected to the threaded rod 24 by a ball and pin connection. For this purpose, a universal joint 104 is provided between the arm 102 and the threaded rod 24. This makes it possible to angularly offset the axis of rotation D1 of the magnet 20 and the axis D2 of the threaded rod 24. This may be advantageous in particular in the case of a bone to be treated that is difficult to access. It is to be noted that even in this case, the magnet 20 remains located near the end 22 of the plate distractor 100, this end 22 being formed in this case by the arm 102.

The functioning of this plate distractor 100 is essentially identical to that of the plate distractor 10. The rotation of the magnet 20, controlled as described above, causes rotation of the arm 102. The rotation of the arm 102 is transferred via the universal joint 104 to the threaded rod 24. As the threaded tube 26 fixed to the second plate 14 cannot rotate at the same time as the threaded rod 24, this rotation of the threaded rod 24 causes the threaded tube 26 to move out of the sleeve 16, thus increasing the distance between the two plates 12, 14.

Figure 5:
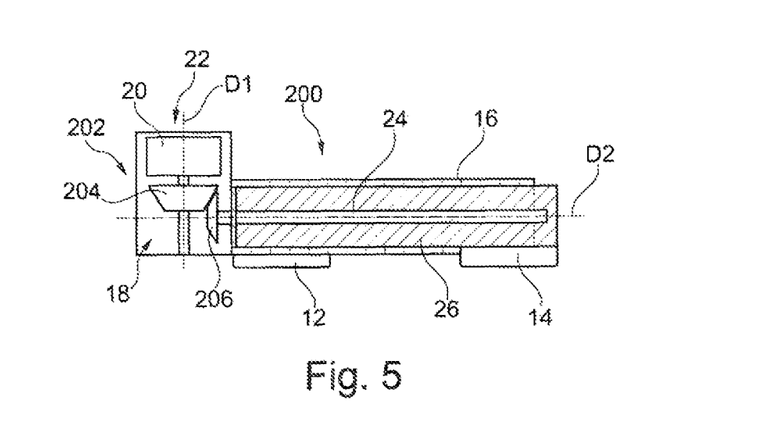
FIG. 5 is a schematic view of a third example of a plate distractor.

The plate distractor 200 of FIG. 5 differs from the plate distractor 10 of FIGS. 1 through 3 in that it comprises an angle gear device 202. Here, in fact, the magnet 20 rotates around an axis of rotation D1 that is essentially perpendicular to the axis D2 of the rod 24. For this purpose, the magnet 20 is mounted in a rotationally fixed manner on a first conical gear 104, which engages a second conical gear 106 rotationally fixed to the rod 24. Of course, other types of gears may be used in this case.

It should be noted here that a reducing effect may be achieved by selecting the number of teeth of the first and second gears 204, 206. In particular, it is possible to achieve a reduction in the rotation speed of the rod 24 in relation to the magnet 20, which is accompanied by an increase in the torque transmitted to the rod 24. This may be advantageous for facilitating extension of the plate distractor 200.

It can be noted here than even in the case of the plate distractor 200, the permanent magnet is located close to one end 22 of the plate distractor 200. In fact, in this case as well, the permanent magnet is located at a distance from the end 22 of the plate distractor 200, measured in the direction of the axis of rotation D1 of the magnet, of less than or equal to 15 mm, preferably less than or equal to 10 mm, more preferably less than or equal to 5 mm. The magnet 20 may even be located at the level of the end 22 of the plate distractor 200, in particular in cases where the magnet is coated with a biocompatible material.

Figure 6:
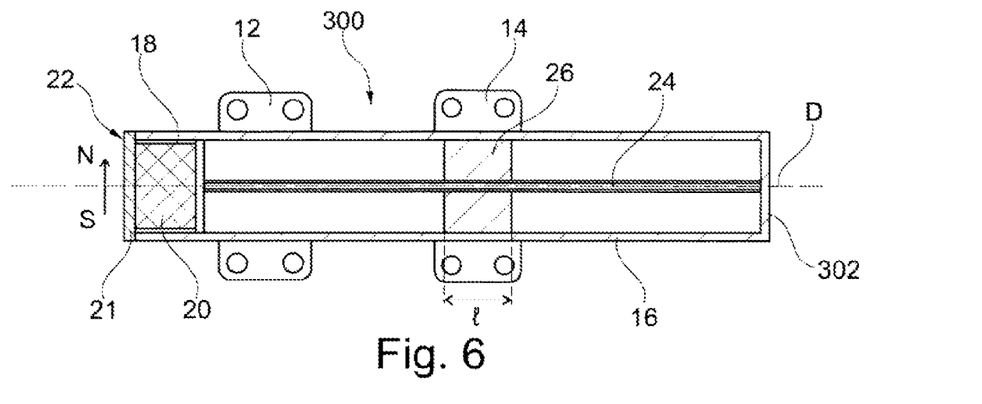
FIG. 6 is a schematic sectional view of a variant of a plate distractor in a partially collapsed configuration.
Figure 7:
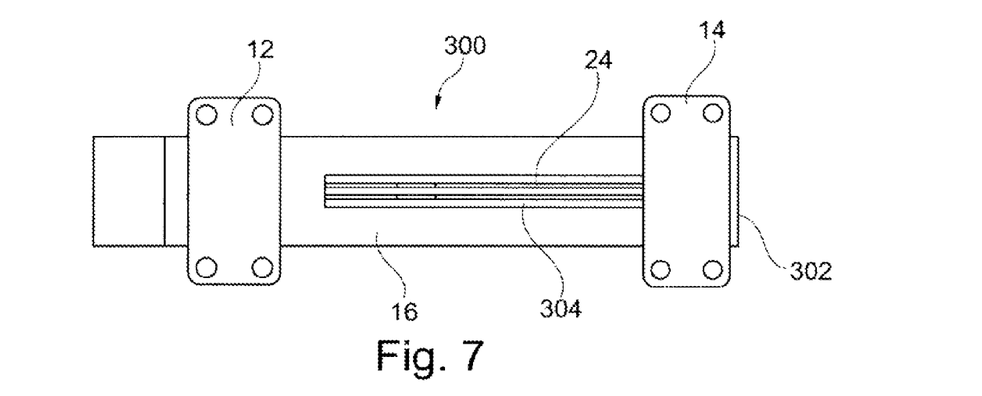
FIG. 7 is a schematic view of the plate distractor FIG. 6 seen from the side of the plates.

The plate distractor 300 of FIGS. 6 and 7 differs from the plate distractor 10 of FIGS. 1 through 3 in that the threaded tube 26 is compact and the sleeve 16 is closed at its end 302 opposite that of the magnet 20. The threaded tube 26 preferably has a width l less than that of the plate on which it is mounted. During rotation of the threaded rod 24, the threaded tube 26 moves translationally along the threaded rod, sliding inside the sleeve 16, which thus serves as a guide. The sleeve 16 comprises a longitudinal opening 304 extending over at least part of the length of the plate distractor and in which the plate 14/threaded tube 26 assembly slides. Such a small threaded tube 26 makes it possible to reduce friction between the tube, the sleeve 16 and the rod 24 during movement of the threaded tube 26.

Figure 8:
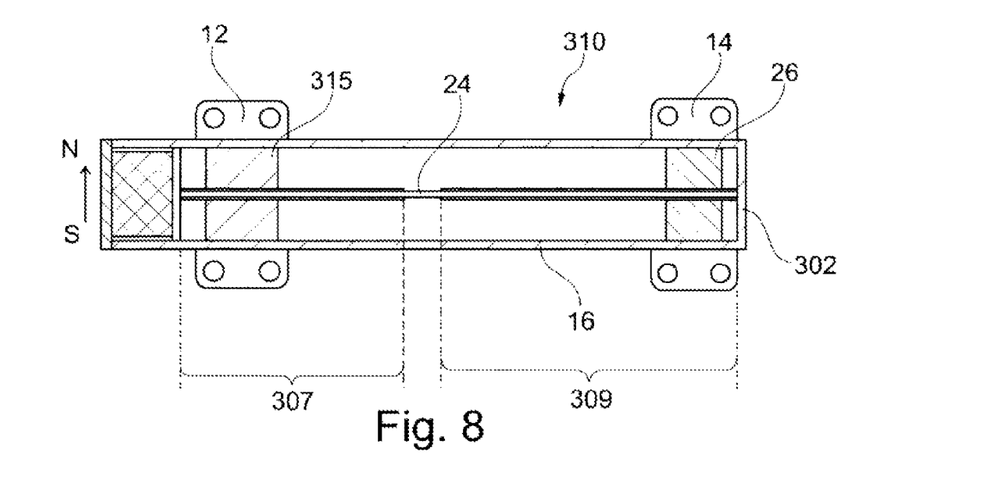
FIG. 8 is a schematic sectional view of a variant of a plate distractor.

The plate distractor 310 of FIG. 8 differs from that of FIGS. 6 and 7 in that a second threaded tube 315 is mounted on the first plate 12 and in that the threaded rod comprises two longitudinal areas 317 and 319 having opposite thread orientations. In this manner, during rotation of the threaded rod, the two tubes 26 and 315 move in opposite directions so as to move the plates 12 and 14 apart or together depending on the direction of rotation.

Figure 11:
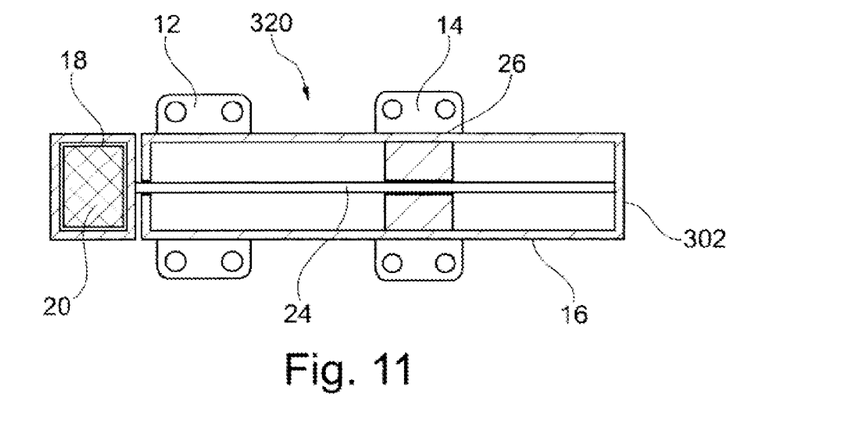
FIG. 11 is a schematic sectional view of a variant of the plate distractor.

The plate distractor 310 of FIG. 11 differs from that of FIGS. 6 and 7 in that the housing 18 is composed of a hermetically sealed case 322 connected to the threaded rod 24 and dissociated from the sleeve 16. During rotation of the magnet 20, the case 322 rotates with the latter at least in one direction and thus causes the threaded rod 24 to rotate. In particular, this type of case makes it possible to protect the magnet from the external environment.

Figure 9:
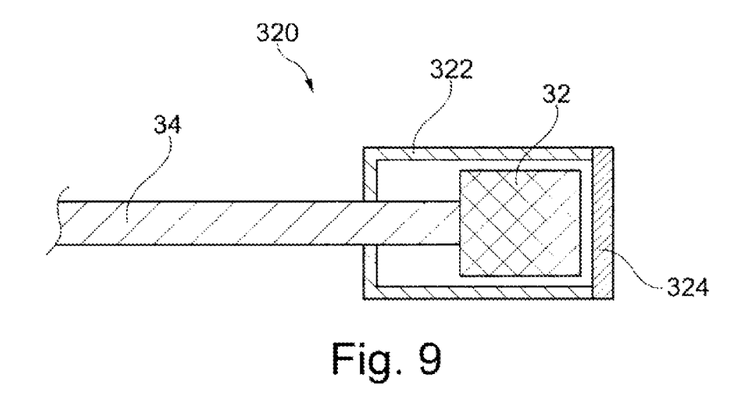
FIG. 9 is a schematic view of an activation tool comprising a magnetic shielding housing in a closed configuration.
Figure 10:
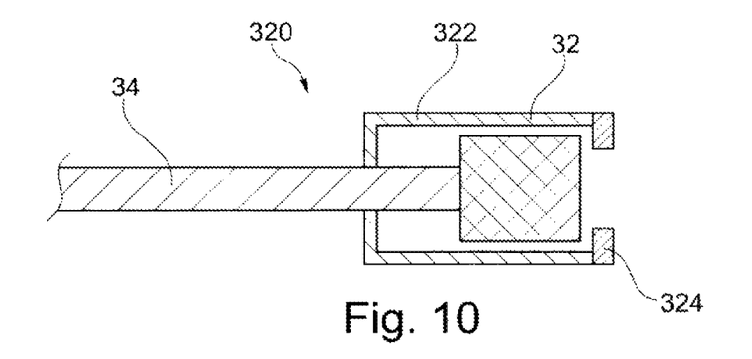
FIG. 10 shows the activation tool of FIG. 9 with the housing in an open configuration.

As shown in FIGS. 9 and 10, the activation tool 320 may comprise a case 322 composed of a magnetic shielding material, in particular Permalloy® or a soft paramagnetic material having at its end 324 a diaphragm which can move from a closed configuration that prevents the magnetic field of the magnet 32 from passing through to an open configuration that at least partially allows the magnetic field of the magnet 32 to pass through.

In this manner, when using the activation tool, the user can position the activation tool in a closed configuration opposite the magnet 20 of the distractor so as to open the diaphragm when the activation tool is properly positioned. This prevents the magnet 32 of the tool from acting on the magnet 20 when this is not desired.

Moving from the closed configuration to the open configuration may be carried out by means of a button, which is not shown, located on the rod 34 of the tool.

Of course, the invention is not limited to the examples described above, but also comprises numerous variants available to the person skilled in the art within the scope of the definition given in the attached claims.

In this manner, the permanent magnet 20 may be rotationally fixed to the threaded tube, and the threaded rod may be mounted in a fixed manner in relation to the sleeve 16.

The second plate 14 may be closer to the permanent magnet than the second plate 12.

The plate distractor may comprise a non-return device that prevents the rotation of the magnet in one direction, thus shortening the distance between the first and second fixing plates. In particular, the non-return device may be of the ratchet type. In fact, this provides the additional advantage of allowing precise control of measurement of the extension of the distance between the first and second plates.

Figure 12:
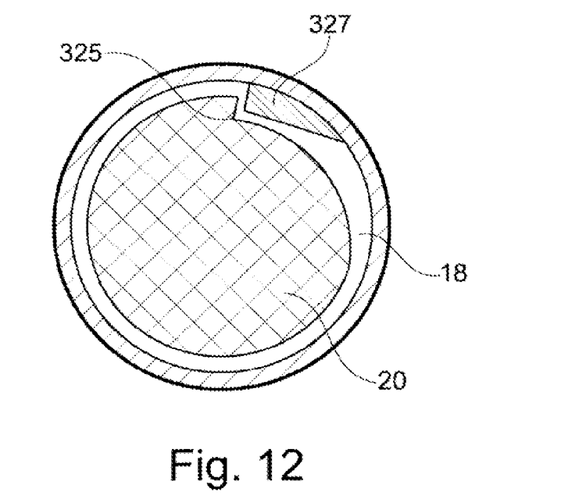
FIG. 12 shows a schematic cross sectional view of a variant of the permanent magnet in its housing.

In a variant shown in FIG. 12, the permanent magnet 20 comprises on its surface an asymmetrical notch 325, and the housing 18 comprises a blade 327, with the notch 325 and the blade 327 being configured such that when the magnet 20 is caused to rotate in a counterclockwise direction, the magnet is freely rotatable in the housing and therefore does not cause the threaded rod to rotate, and when the magnet 20 is caused to rotate in a clockwise direction, the blade 327 engages with the notch 325 and the housing 18 is caused to rotate with the magnet 20, which causes the threaded rod 24 to rotate.

In a further alternative, the non-return system may be adapted to the activation tool such that the latter can turn in only one direction.

Moreover, the plate distractor may comprise a reduction device, in particular for increasing the torque between the rod and the threaded tube. In particular, this reduction device may comprise one or a plurality of toothed wheel gears. It should be noted here that in cases where a reduction device is provided, it is preferable for reasons of compactness for the axis of rotation of the permanent magnet to remain essentially parallel to the axis of the threaded rod.

Moreover, the plate distractor according to the invention may comprise a device for determining the extension length of the distractor. This device thus makes it possible to verify for each extension effected that the extension in question is in accordance with the desired extension value. A ratchet device can thus be provided such that rotation of the threaded rod in relation to the tube causes clicks to be heard. The number of clicks can be counted in order to determine the extension effected. The device for determining the extension length may be independent of the non-return device. Alternatively, however, a single ratchet device may make it possible to simultaneously determine the extension length of the distractor and prevent rotation of the threaded rod in one direction, thus controlling the narrowing of the distance between the plates of the distractor.

More generally, the device for determining the extension length may be configured to emit a sound on completion of each turn or part of a turn, in particular each half turn or quarter turn.

Finally, the plate distractor may comprise more than two plates. In particular, it may comprise three plates, for example in the technique referred to as "bone transport" distraction. In this case, two of the plates are attached on either side of the osteotomy line as described above. The third plate is then attached to the threaded tube on the one hand and to the bone on the other on either side of the osteotomy line.

The invention claimed is:

1. A distractor assembly comprising:
   a plate distractor comprising:
      a first and a second fixing plate,
      a threaded rod
      a threaded tube mounted on the threaded rod and attached to the second fixing plate,
      a sleeve accommodating the threaded rod that is freely rotatable and translatably fixed relative to the sleeve and the threaded tube that is freely translatable and rotatably fixed relative to the sleeve,
      a permanent magnet accommodated in a housing, extending in a main direction and magnetized transverse to the main direction, mounted in the plate distractor such that the rotation of the magnet on itself around an axis of rotation parallel to the main axis causes a relative rotation of the threaded rod in relation to the threaded tube, with the magnet being located at a distance from one of the ends of the plate distractor, measured in the direction of the axis of rotation of the magnet, of less than or equal to 15 mm,
   an activation tool of the plate distractor comprising a permanent magnet extending in a main direction and magnetized transverse to the main direction, configured to be placed opposite the magnet of the plate distractor such that their magnetization directions are essentially parallel and causing the magnet of the plate distractor to rotate by rotating the magnet of the activation tool around an axis that is essentially colinear with the axis of the permanent magnet of the distractor.

2. The assembly according to claim 1, wherein the magnet of the distractor is located at one end of the plate distractor.

3. The assembly according to claim 1, wherein the magnet of the plate distractor is cylindrical.

4. The assembly according to of claim 1, the plate distractor comprising an angle gear device such that the axis of rotation of the magnet is essentially perpendicular to the axis of the threaded rod and of the threaded tube.

5. The assembly according to claim 4, wherein the angle gear device comprises a first gear rotationally fixed to the magnet and adapted to engage with a second gear controlling the rotation of one of the threaded rod and the threaded tube.

6. The assembly according to claim 1, wherein the magnet is connected to the threaded rod or the threaded tube by a reduction device.

7. The assembly according to claim 4, wherein the angle gear device comprises a first gear rotationally fixed to the magnet and adapted to engage with a second gear controlling the rotation of one of the threaded rod and the threaded tube and the reduction device includes the first and second gears.

8. The assembly according to claim 1, the plate distractor comprising an arm connected to the threaded tube by a ball and pin connection, wherein the ball and pin connection is implemented by means of a universal joint, the universal joint being provided between the arm and the treaded rod.

9. The assembly according to claim 1, wherein the magnet of the plate distractor is rotationally fixed to the threaded rod or the threaded tube.

10. The assembly according to claim 1, the plate distractor comprising a non-return device that prevents the rotation of the magnet of the plate distractor in one direction, controlling a reduction in the distance between the first and second plates.

11. The assembly according to claim 1, wherein the magnet of the plate director is composed of neodymium or neodymium alloy, samarium or samarium alloy, ferrite or ferrite alloy.

12. The assembly according to claim 1, wherein at least one of the threaded tube, the first plate and the second plate is/are composed of titanium or titanium alloy.

13. The assembly according to claim 1, wherein the housing is attached to the threaded rod.

14. The assembly according to claim 1, wherein the threaded tube has a width less than or equal to the width of the second plate.

15. The assembly according to claim 1, wherein the permanent magnet of the plate distractor is such that its magnetization is retained when it is heated to a temperature of 120° C.

16. The assembly according to claim 1, wherein the threaded rod is mounted in a freely rotatable and translatably fixed manner in relation to the first fixing plate.

17. The assembly according to claim 1, wherein the threaded rod comprises two longitudinal areas having opposite threads, with the first threaded tube to which the second plate is attached being mounted on one of the two longitudinal areas and a second threaded tube to which the first plate is attached being mounted on the other of the two longitudinal areas.

18. The assembly according to claim 1, wherein the magnet and the housing are configured such that the magnet is freely rotatable in the housing when it rotates in a first direction and the magnet rotationally drives the housing and thus the threaded rod when it rotates in a second direction.

19. The assembly according to claim 1, the plate distractor comprising a device for determining the extension length of the distractor.

20. The assembly according to claim 1, the housing being hermetically sealed.

21. The assembly according to claim 1, wherein the activation tool comprises a magnetic shielding housing wherein the magnet is accommodated, with the magnetic shielding housing being capable of moving from a closed configuration in which the shielding of the magnetic field is sufficient to prevent the rotation of the magnet of the activation tool around the main direction from causing rotation of the magnet of the plate distractor around its axis to an open configuration in which the rotation of the magnet of the activation tool around the main direction causes the rotation of the magnet of the plate distractor around its axis and vice versa.

22. The distraction assembly according to claim 1, wherein the magnet of the activation tool is cylindrical.

23. The assembly according to claim 1, the magnet being located at a distance from one of the ends of the plate distractor, measured in the direction of the axis of rotation of the magnet, of less than or equal to 10 mm.

24. The assembly according to claim 18, the magnet comprising an asymmetrical notch and the housing comprising a projection cooperating with the notch such that the magnet is free to rotate in the first direction and the projection engages with the notch in the second direction.

* * * * *

UNITED STATES PATENT AND TRADEMARK OFFICE
CERTIFICATE OF CORRECTION

PATENT NO. : 10,736,664 B2
APPLICATION NO. : 16/060689
DATED : August 11, 2020
INVENTOR(S) : Strozyk et al.

It is certified that error appears in the above-identified patent and that said Letters Patent is hereby corrected as shown below:

On the Title Page

Item (73) should read:
(73) Assignee:
ECOLE NATIONALE SUPERIEURE DE TECHNIQUES AVANCEES,
Palaiseau (FR)
ASSISTANCE PUBLIQUE - HOPITAUX DE PARIS,
Paris (FR)
UNIVERISITE PARIS DESCARTES,
Paris (FR)
ECOLE POLYTECHNIQUE,
Palaiseau (FR)

Signed and Sealed this
Eleventh Day of January, 2022

Drew Hirshfeld
*Performing the Functions and Duties of the*
*Under Secretary of Commerce for Intellectual Property and*
*Director of the United States Patent and Trademark Office*